United States Patent [19]
Onda et al.

[11] Patent Number: 5,198,542
[45] Date of Patent: Mar. 30, 1993

[54] DNA ENCODING A PITUITARY ADENYLATE CYCLASE ACTIVATING PROTEIN AND USE THEREOF

[75] Inventors: Haruo Onda, Ibaraki, Japan; Akira Arimura, New Orleans, La.; Chiharu Kimura, Ibaraki; Chieko Kitada, Osaka, both of Japan

[73] Assignee: Takeda Chemical Industries, Inc., Osaka, Japan

[21] Appl. No.: 540,105

[22] Filed: Jun. 10, 1990

[30] Foreign Application Priority Data

Jun. 20, 1989 [JP] Japan .................................. 1-155791
Oct. 6, 1989 [JP] Japan .................................. 1-259924
Nov. 2, 1989 [JP] Japan .................................. 1-284771
Feb. 22, 1990 [JP] Japan .................................. 2-39841

[51] Int. Cl.$^5$ .................................................. C07G 15/12
[52] U.S. Cl. ................................. 435/69.4; 435/69.1; 435/320.1; 435/252.33; 536/23.51; 536/23.5; 530/324
[58] Field of Search .............. 536/27; 435/69.1, 320, 435/252.33, 69.4

[56] References Cited

PUBLICATIONS

Tatsuno et al., *Endocrinology* 129(4):1797–1804 (1991).
Kimura et al., *Biochem and Biophys Res Comm.* 166(1): pp. 81–90(1990).
Miyata, et al., 71st Annual Meeting of the Endocrine Society, Seattle, Washington, Jun. 21–24, 1989. Abstract #168.
Arimura, et al., 71st Annual Meeting of the Endocrine Society, Seattle, Washington, Jun. 21–24, 1989. Abstract #964.

*Primary Examiner*—David Lacey
*Assistant Examiner*—Shelly J. Guest
*Attorney, Agent, or Firm*—David G. Conlin; Ronald I. Eisenstein

[57] ABSTRACT

Disclosed are (1) a DNA containing a DNA segment coding for PACAP38; (2) a precursor protein of PACAP38; (3) a transformant containing a DNA having a DNA segment coding for PACAP38; (4) a method of preparing mature PACAP38 comprising cultivating the transformant described in the above (3), producing and accumulating a protein in a culture, and collecting the resulting protein; and (5) a method for preparing the above polypeptide comprising condensing a partial amino acid or a peptide which can constitute the mature PACAP38, with a residual portion, and removing a protective group if a product has the protective group. The DNA is applied to experimental animals to understand their brain functions, which serves to elucidate human brain functions. PACAP38 provides information about growth and maintenance of rat and human brain nerves, and can also be utilized as therapeutic agents for various neuropathy.

18 Claims, 6 Drawing Sheets

A HUMAN CANDIDATE CLONE

```
  1  CTGCTAACTGCCCAGATAAATAGGAGCAGAGGGCTGGTCACCTCTGTAATAACCACCGGCAGCAGTAGAAGAAAC   75
 76  CGCAGCTTCAGAAGCAGCCAGAGACTTCTGAGCAGCCCCTCTCTCTCTCTCTCTCTCTCTGGCCGGGCGGCTGCC  154
155  CCAGACGCCGACTTCGCCGAGGCCCTCTCTCTCTCAGTGGACTTCAGGCCACTTGTCTCCACCCCACTCAGTCGCGCCTCCCGTCTT  233
234  CTTATCACTCCTTCTTTCTTCAGTGGACTTCAGGCCACTTGTCTCCACCCCACTCAGTCGCGCCTCCCGTCTT  312
313  CCCTTCTCCATCTCTCGCCCCCCTCTCTCAGTGTCACGCTCCAGTTCCGAGCTGTCAAACTTTGAA  391
392  CAGAATAACAGGACTCAGCAACAAGTCCTCCAGCTCCTCCCCGGCTCCGTCTTCCTGGGCTCGTCCTGCTCAGACA  470
471  CTAACGCCAGACGGCGATGCCTCTTGGGTTGTGACTACAGCGGCACAAACTTGGAGAAGCTCTTTGCCCGCCGTCCTACT  549

550  TGGCAGCAAATCCTCTGGCAGCGA ATG ACC ATG TGT AGC GGA GCG AGG CTG GCC CTG CTC GTT  615
                              Met Thr Met Cys Ser Gly Ala Arg Leu Ala Leu Leu Val   13

616  TAC GGG ATA CTG ATG CAC AGC AGC GTC TAC AGC TCA CCT GCC CTC GGA CTC CGG TTC  675
 14  Tyr Gly Ile Leu Met His Ser Ser Val Tyr Ser Pro Ala Leu Gly Leu Arg Phe      33

676  CCG GGG ATC AGG CCG GAG AAC GAG TAC GAC GCG GGA AAC CCG CAG GAG GAC TTC      735
 34  Pro Gly Ile Arg Pro Glu Asn Glu Tyr Asp Ala Gly Asn Pro Gln Glu Asp Phe      53

736  TAC GAC TCG GAG CCG CCA GGC GTG GGG AGC CCC GCC TCC GCG GAT GCC TAC GCG      795
 54  Tyr Asp Ser Glu Pro Pro Gly Val Gly Ser Pro Ala Ser Ala Asp Ala Tyr Ala      73

796  CTC TAC TAC TAC CCG GCG GAG GAA GAT GTC GCC CAC GGG ATC CTT GAT AAG GCC TAC CGC  855
 74  Leu Tyr Tyr Tyr Pro Ala Glu Glu Asp Val Ala His Gly Ile Leu Asp Lys Ala Tyr Arg  93

856  AAA GTG CTG GAC CAG CTG TCC GCC AGA TAC CTG CAG ACG ATG GCC AAG GGC TTG  915
 94  Lys Val Leu Asp Gln Leu Ser Ala Arg Tyr Leu Gln Thr Met Ala Lys Gly Leu  113

916  GGT GGG ACC CCG GGC GGC GGC GAC GAC GAC TCG GAG CCG CTC TCC AAG CGC CAC TCG  975
114  Gly Gly Thr Pro Gly Gly Gly Asp Asp Asp Ser Glu Pro Leu Ser Lys Arg His Ser 133
```

FIG.2-1

```
 976 GAC GGC ATC TTC ACT GAC AGC CGC TAC AGC CGC AAG CAA ATG GCT GTT AAG AAA TAC 1035
 134 Asp Gly Ile Phe Thr Asp Ser Arg Tyr Ser Arg Lys Gln Met Ala Val Lys Lys Tyr  153

1036 TTG GCG GCT GTC CTA GGG AAA AGG TAT AAA CAA AGG GTT AAG AAC AAA GGA CGG CGA ATA 1095
 154 Leu Ala Ala Val Leu Gly Lys Arg Tyr Lys Gln Arg Val Lys Asn Lys Gly Arg Arg Ile  173

1096 CCG TAC TTG TAG CGACGAGTTACCAGCTATCCTGTGTATACAGCCCTGACACAATGAGAAGTCGTTTTCCCAAC 1170
 174 Pro Tyr Leu ***                                                                  177

1171 TGACTGAACTGTCATCGCTGCTGTCTCTGTCCCACATGTATTTATGAAGTCAAGCCATTAAATGAATATTTGA 1249
1250 TAATAATATTGTTTTTCTTTTTACGAAGCACTGGAGAATGCACAGATATACTTTGTGGACCAATTATTGATATTGACAT 1328
1329 ATATATTACGAATATATAAAGAGTATATATATATAAGTATATATAATAGAGAGCCGTTCATACAGTGTGCACAAGGA 1407
1408 CTGAAGATTCGCCTGAGCTGTTTGTTTTTATATAAAATAAAATAGAAAAAATAGACAATCATTGTTTTGAATATTACTCCT 1486
1487 ATTTTTGTAAACTGGAATTAAAAGGATAGTATTTTTATCCACAATAGGCCTGAAGATATTAATCCTGACCATTTGCTAC 1565
1566 TGTACATAAACAGTGATGCCCTGCTCCAGGGAGACTTTGAGGTAATGATTTGGGAGGATTGCTGAAGGTCTCTCTTTCC 1644
1645 CAGGGAGTCTCGGGGCAGGCTGCTTCAATCCCAGCTGAACTCGACTGAGGCTCTGTCTACCCCTTGCTGGGTGGCAAT 1723
1724 GCCAATACTTCCGCTTTCTTTGATTCTATTTTATGTGTA 1763
```

FIG.2-2

```
A ATG ACC ATG TGT AGC GGA GCG AGG CTG GCC CTG GTC TAT GGG ATA ATC ATG CAC AGC GTC TAC
  Met Thr Met Cys Ser Gly Ala Arg Leu Ala Leu Val Tyr Gly Ile Ile Met His Ser Ser Val Tyr

GAA GAG GCG TAC GGC GAG GAC GGA AAC CCG CTG CCA GAC TTC GGT GGC GGC TCG GAG CCG GGC GCA GGG AGC
Glu Glu Ala Tyr Gly Glu Asp Gly Asn Pro Leu Pro Asp Phe Gly Gly Ser Glu Pro Pro Gly Ala Gly Ser

AGA AGA GAT GTC GCC CAC GGG ATC CTT AAC GAG GCC TAC CGC AAA GTG CTG GAC CAG CTG TCC GCC GGG AAG
Arg Arg Asp Val Ala His Gly Ile Leu Asn Glu Ala Tyr Arg Lys Val Leu Asp Gln Leu Ser Ala Gly Lys

GGC GCG GAC GAC GCG GAG CCG CTC TCC AAG CGC CAC TCG GAC GGG ATC TTC ACG GAC TAC AGC CGC
Gly Ala Gly Asp Asp Ala Glu Pro Leu Ser Lys Arg His Ser Asp Gly Ile Phe Thr Asp Tyr Ser Arg

AAG AGG TAT AAA CAA AGG GTT AAA AAC AAA GGA CGC CGA ATA GCT TAT TTG TAGCGATGGGTTACCAGCTACCCTGT
Lys Arg Tyr Lys Gln Arg Val Lys Asn Lys Gly Arg Arg Ile Ala Tyr Leu *

TCAACAGTCATCGCTCGTGTTCTATCCAAACATGTATTTATGTAATGAAGTAAAGCCATTAAATGAATATTTTGATAATAATATATTGTTTTC
AGATATACTTTGTGGACCAATTATTGATATATATATATAAATATATAAAGAATATATATATATAAAGTATAGAGAAGTTCA
TTCGCCCGAGCTGTTTATGTTTTATAAAAATAAATAGAAAAGTAGACAATCATTGTTTGAATATTACTCCTATTTTTGTAAACTGGAATTAA
GCCTGAAGATATTACTACTTGCTACTGTACATAAACAATGATGCCCTGCTCCAGGGAGATTTGAGGTAAAGATATGGAGAATTGCT
CTGGGGCAGGCTGCTTCAATCCCAGCCTAACTCAACAGTCTGTCCCCCTGGTTGGGTGGCAATTCCAATATTTCTGCTTTCTTTGATTCTC
GACTCTCAGCCCAGAAGAAAATTCTCCTGATAAAACAACAGCTCGATCCAAATTGTGCTTCTCCCCAGAATTCACGCCTCTCCCTAGGAGAAGA
GCTTCGTTAGACCGCTCTCTTTTCTGTACTTCCTGAGTGGCCAGGAATCTAATATCCCAAATTAGGCAATTGAACAAAGTGAAGGACATA
GAGGTGGTAGGAGGAGACCCTGGAAATGGACTGGTTTGAGATTGCCCCAGGTCTGAGGGCAAATCCCAGTCCCAGTCTGACT
GCAAAGTACAATGTGTTTTCTCCAGTGCTTCTCCATGCTTCTCATCTTGTGAAATGGCCAGGATCCTCTCTTGAAACCTGCTCTGTAGGAGC
AGACCTCTCCTTCCTACCCTCCGACTGTTAAGTAGTACTGTTTACCATTTTCATTCACTTCTCTTAAACTTGTGAATGCTTCTCACTTTTT
AAATTTTAGAAACCCTCTGTAGCCACTAGTAAGTAATTATGCACTAAATATGAACCCTTTGTTTTCTTGTTTATTGAGTTTGTAGGTAAAATGT
TAGTAAATTTATTTCATAAAA
```

FIG. 4-I

```
AGC TCA CCT GCC GCC GGA CTC CGG TTC CCC GGG ATC AGG CCA GAG    118
Ser Ser Pro Ala Ala Ala Gly Leu Arg Phe Pro Gly Ile Arg Pro Glu 39

CCC GCC TCC GCG CCG CGC GCC GCC GCC TGG TAC CGC CCG GCC GGG    238
Pro Ala Ser Ala Pro Arg Ala Ala Ala Trp Tyr Arg Pro Ala Gly    79

CAC CTG CAG TCG CTC GTG GCC CGG GTG GGC GGT GGG AGC CTC GGC GGC   358
His Leu Gln Ser Leu Val Ala Arg Val Gly Gly Gly Ser Leu Gly Gly  119

TAC CGG AAA CAA ATG GCT GTC AAG AAG TAC TTG GCG GCC GTC CTA GGG   478
Tyr Arg Lys Gln Met Ala Val Lys Lys Tyr Leu Ala Ala Val Leu Gly  159

TATACAGCCCTGACGCAATGAAAAGTCGTTTCCAAACTGAC    598
                                            176

TTTCTACAAAGCACTAGAGAATGCAC                  718

TACAAAGCGTGCACAAGGATTGAAA                   839

AAGGATAGTATTTTTATCCATGACAG                  958

GAAGGGCATTCTTTCCCAGTGAGTCT                  1078

CTTTTATGTGTAGTTGTCTCTCTTCA                  1198

GTTGAGGAACTGTACAGAAAAGGGCG                  1318

GAGGTATATTGGAAGAGGCAGAGCCT                  1438

TTGGGGCTGGGTATTGGAAATGGAT                   1558

TACCCTTTCCTTTGTGTTTTATGG                    1678

TTTGTTGATGCAGGCACTTATTGT                    1798

ATTTTCTACATTATTGCTTATTGCT                   1918

```
  1 GAATTCAGGACTCTCAAAGCTCCACAATGGCGCCCAGCTCTCTCCTCAGCAACAGACTGAAGGCTTCGGCTAGTTTTGT   79

80 GCGTCTACAAAGCTTTGAGCGGAATTTTAGCTTCGGCAAACAAGTCCCCCCAGCTCCTCCAGCTAATTCCCGCGACTTCT  159

160 CTCCAGACACCAGCTCCAGACAGTGACTGATGCCTCTCTGGTTGTGATTCCAGCGCAGAAACTCGAAGGAGCCCTTTGCC  239

240 CGCCGTCCTATTTAGTCAACTCTTTCCTAGCCGCGA ATG ACC ATG TGT AGC GGA GCA AGG TTG GCC CTG  308
  1                                      Met Thr Met Cys Ser Gly Ala Arg Leu Ala Leu   11

309 TTG GTC TAC GGG ATA ATA ATG CAT AAC AGC GTC TCC TGT TCA CCT GCC GCC GGA CTC AGC  368
 12 Leu Val Tyr Gly Ile Ile Met His Asn Ser Val Ser Cys Ser Pro Ala Ala Gly Leu Ser   31

369 TTC CCT GGG ATC AGA CCA GAA GAA GAG GCT TAC GAT CAG GAC GGA AAC CCG CTG CAA GAC  428
 32 Phe Pro Gly Ile Arg Pro Glu Glu Glu Ala Tyr Asp Gln Asp Gly Asn Pro Leu Gln Asp   51

429 TTC TAC GAC TGG GAC CCT CCG GGC GCA GGG AGC CCC GCC TCC GCG CTG CGT GAC GCC TAC  488
 52 Phe Tyr Asp Trp Asp Pro Pro Gly Ala Gly Ser Pro Ala Ser Ala Leu Arg Asp Ala Tyr   71

489 GCC CTT TAC TAC CCA GCC GAC AGG AGA GAT GTC GCC CAC GAA ATC CTT AAC GAA GCC TAC  548
 72 Ala Leu Tyr Tyr Pro Ala Asp Arg Arg Asp Val Ala His Glu Ile Leu Asn Glu Ala Tyr   91

549 CGC AAA GTC TTG GAC CAG CTG TCC GCC AGG AAG TAC CTG CAG TCC ATG GTG GCC AGG GGC  608
 92 Arg Lys Val Leu Asp Gln Leu Ser Ala Arg Lys Tyr Leu Gln Ser Met Val Ala Arg Gly  111

609 ATG GGC GAG AAC CTC GCC GCC GCC GCG GTG GAC GAC CGG GCA CCC CTT ACC AAA CGC CAC  668
112 Met Gly Glu Asn Leu Ala Ala Ala Ala Val Asp Asp Arg Ala Pro Leu Thr Lys Arg His  131

669 TCG GAC GGC ATC TTC ACA GAC AGC TAT AGC CGC TAC CGA AAA CAA ATG GCT GTC AAG AAA  728
132 Ser Asp Gly Ile Phe Thr Asp Ser Tyr Ser Arg Tyr Arg Lys Gln Met Ala Val Lys Lys  151

729 TAC TTG GCG GCC GTG CTA GGG AAA AGG TAT AAA CAG AGG GTT AAA AAC AAA GGA CGC CGA  788
152 Tyr Leu Ala Ala Val Leu Gly Lys Arg Tyr Lys Gln Arg Val Lys Asn Lys Gly Arg Arg  171

789 ATA GCG TAC TTG TAG CGATGAGTTGCCAGCTACCGTGTGTATAAAATGAAAAGTCGTTTTCCAAATTGACTGACC  863
172 Ile Ala Tyr Leu ***                                                               176

864 AGTCATCACTCATGTGTTCTTTCCAAACATGTATTTATGTATCAAGTAAAGCCATTAAATGACTATTTTGATAATAATAT  943

944 TGTTTTTCTTTTTACGAAGCACTGGAGAATGCACAGATATACTTTGTGGACCAATTATTGATATATATTATAAGTATATA 1023

1024 TTAAGAATATATATAGGTATAGCAGAGAGCAATTCATAAGCGTGCACAAAGATTGAAAATTCGCCTGACGCTGTTTATGT 1103

1104 TTTATATAAAATGAATAGAGAAAATAGACAACCATTGTTTTGAATATTACTCCTATTTTTGTAAACTGGAATTAAAGGAT 1183

1184 AGTATTTTTATCCACAACCGGCTTGAAGATACCAATAATGGCCATTTGTACAAAAAAATGATGCCCTGCTCCAGGAGAAT 1263

DNA ENCODING A PITUITARY ADENYLATE CYCLASE ACTIVATING PROTEIN AND USE THEREOF

BACKGROUND OF THE INVENTION

The present invention relates to a novel bioactive peptide derived from brain hypothalami, testes or the like, a DNA containing a DNA segment coding for the peptide, a transformant bearing the DNA, and a method for preparing the above peptide by using the transformant.

Various hormones secreted by brain hypothalami and hypophyses have been known. Examples thereof include thyrotropin releasing hormone, luteinizing hormone releasing hormone, somatostatin, adrenocorticotropic hormone, growth hormone and prolactin. Action thereof has been well studied. One of the present inventors studied a certain novel bioactive substance of hypothalamic origin other than these hormones based upon adenylate cyclase activity, and consequently discovered a peptide consisting of 38 amino acid residues, which had not been reported till then. The structure thereof was determined and the peptide was named "PACAP38".

The present inventors filed applications for patents (Japanese Patent Application Nos. 1-155791/1990 and 1-284771/1990) on cDNA of sheep PACAP38, and an application for a patent (Japanese Patent Application No. 1-259924/1990) on the partial structure of cDNA of human PACAP38. It was also discovered that the amino acid sequence of the mature portion of sheep PACAP38 was the same as that of human PACAP38, and that some amino acids of the precursors thereof were substituted.

However, although the existence of the PACAP38 peptides was confirmed as described above, it is difficult to isolate and purify the peptides and their precursors from hypothalami or the like, because of the necessity of very complicated operations, and that the desired peptides are obtained only in small amounts. It has therefore been desired to provide a method for obtaining the peptides easily and in large amounts.

SUMMARY OF THE INVENTION

The present inventors have studied mass-production techniques for producing the PACAP38 peptides. As a result, the present inventors have succeeded in isolating a cDNA coding for a PACAP38 peptide from a cDNA library prepared from a messenger RNA of rat brain origin and in determining its nucleotide sequence, from rats as well as from sheep and humans. We discovered that the amino acid sequences of these three kinds of PACAP38 mature proteins are the same, and this has made it possible to obtain the PACAP38 peptides in large amounts by using genetic engineering techniques, thus arriving the present invention.

The amino acid sequences of the PACAP38 mature protein is represented by formula (1):

[Formula 1]
His Ser Asp Gly Ile Phe Thr Asp Ser Tyr Ser Arg Tyr Arg

Lys Gln Met Ala Val Lys Lys Tyr Leu Ala Ala Val Leu Gly

Lys Arg Tyr Lys Gln Arg Val Lys Asn Lys

In accordance with the present invention, there are provided (1) a DNA containing segment coding for PACAP38; (2) a precursor protein of PACAP38; (3) a transformant bearing a DNA containing a DNA segment coding for PACAP38; (4) a method for preparing mature PACAP38 comprising cultivating the transformant described in the above (3), producing and accumulating a protein in a culture product, and collecting the resulting protein; and (5) a method for preparing the above polypeptide comprising condensing a partial amino acid or a peptide which can constitute mature PACAP38, with a residual portion, and removing a protective group if a product has the protective group.

BRIEF DESCRIPTION OF THE DRAWINGS

FIGS. 2-1-2-2 shows a nucleotide sequence of the cDNA coding for a portion of a sheep PACAP38 precursor and the deduced amino acid sequence of that portion of the sheep PACAP38 precursor;

FIGS. 4-1-4-2 shows a nucleotide sequence of the cDNA coding for a portion of a human PACAP38 precursor and the deduced amino acid sequence of the human PACAP38 precursor;

FIG. 6-1-6-2 shows a nucleotide sequence of the cDNA coding for a portion of a rat PACAP38 and the deduced amino acid sequence of that rat PACAP38 precursor.

DESCRIPTION OF THE PREFERRED EMBODIMENTS

Figure 1:
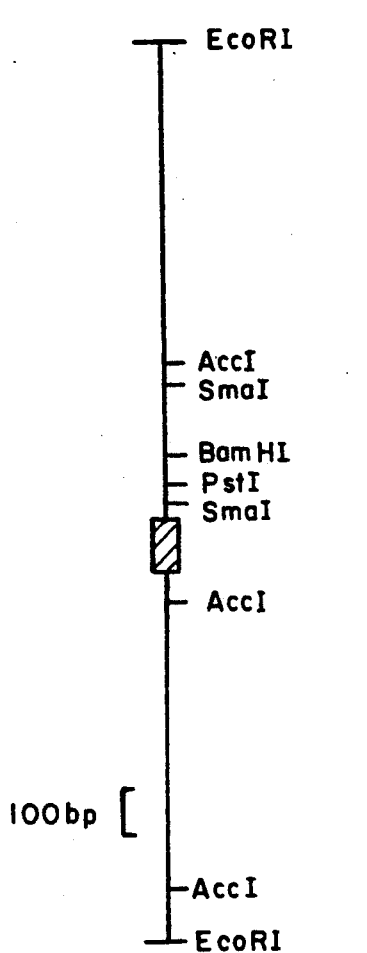
FIG. 1 is a simplified restriction enzyme map of the cDNA coding for a portion of a sheep PACAP38.

In the present invention, the DNAs containing the DNA segments coding for sheep PACAP38 include a DNA containing a nucleotide sequence substantially corresponding to formula (2) or (3) and a DNA substantially corresponding to a portion thereof. More preferably the DNA is represented by formula (2) or (3) or a portion thereof.

[Formula (2)]
5'  CAC TCG GAC GGC ATC TTC ACT GAC AGC TAC

AGC CGC TAC CGG AAG CAA ATG GCT GTT AAG AAA

TAC TTG GCG GCT GTC CTA GGG AAA AGG TAT AAA

CAA AGG GTT AAG AAC AAA GGA CGG CGA ATA CCG

TAC TTG TAG CGA CGA GTT ACC AGC TAT CCT

[Formula (3)]
1   CTGCTAACTGCCCAGATAAATAGGAGCAGAGGGCTGGTCAC
CTCTGTAATAACCACCGGCAGCAGTAGAAGAAACCGCAGCTTCA
GAAGCAGCCAGAGAGACTTCTGAGCAGCGAAGGCGCTGCCTGCT
CGAGCTGCCTGGCCGGGCGGCTGCCCCAGACGCCGACTTCGCCG
AGGCCCTCTCTCTCTCTCTCTCTCTCTCTCTCTCTCTCTCTCTC
TCTCTCTGCTTCTTTCCTTATCACTCCTTTCTTCTCAGTGGACT
TCAGGCCACTTTGTCTCCCACCCCCACTCAGCTCGTCGCCTCCT
CCGTCTTCCTTCTCCATCTCTCCTCTCGCCCCCCTTCTCTCAGT
GTCACGCTCCGTCCTAGTTCCGAGCGTCGTCAAACTTTTGAACA
GAATAACAGGACTCAGCAAACAAGTCCTCCAGCTCCTCCCGCGG
CTCCGGCTCGTTCCTGCGGCTCCTGCTCAGACACTAACGCCAGA
CGGCGATGCCTCTTGGGTTGTGACTACAGCGCACAAACTTGGAG
AAGCTCTTTGCCCGCCGTCCTACTTGGCAGCAAATCCTCTCCTG GCAGCGA ATG ACC ATG TGT AGC GGA GCG AGG CTG
GCC CTG CTC GTT TAC GGG ATA CTG ATG CAC AGC
AGC GTC TAC GGC TCA CCT GCC GCC TCC GGA CTC
CGG TTC CCG GGG ATC AGG CCG GAG AAC GAG GCG
TAC GAC GAG GAC GGA AAC CCG CAG CAG GAC TTC
TAC GAC TCG GAG CCG CCA GGC GTG GGG AGC CCC
GCC TCC GCG CTG CGC GAT GCC TAC GCG CTC TAC
TAC CCG GCG GAG GAA AGA GAT GTC GCC CAC GGG
ATC CTT GAT AAG GCC TAC CGC AAA GTG CTG GAC
CAG CTG TCC GCC AGG AGA TAC CTG CAG ACG CTC
ATG GCC AAG GGC TTG GGT GGG ACC CCG GGC GGC
GGC GCG GAC GAC GAC TCG GAG CCG CTC TCC AAG
CGC CAC TCG GAC GGC ATC TTC ACT GAC AGC TAC
AGC CGC TAC CGG AAG CAA ATG GCT GTT AAG AAA
TAC TTG GCG GCT GTC CTA GGG AAA AGG TAT AAA
CAA AGG GTT AAG AAC AAA GGA CGG CGA ATA CCG
TAC TTG TAG CGACGAGTTACCAGCTATCCTGTGTATACAGC
CCTGACACAATGAGAAGTCGTTTTTCCCAACTGACTGAACTGTC
ATCGCTGCTGTGTTCTGTCCCACATGTATTTATGTATGAAGTCA
AGCCATTAAATGAATATTTTGATAATAATATTGTTTTTCTTTTT
ACGAAGCACTGGAGAATGCACAGATATACTTTGTGGACCAATTA
TTGATATTGACATATATATTACGAATATATAAAGAGTATATATA
TATATATATAAGTATAATAGAGAGCCGTTCATACAGTGTGCACA
AGGACTGAAGATTCGCCTGAGCTGTTTGTTTTTATATAAAATAA
ATAGAAAAATAGACAATCATTGTTTTGAATATTACTCCTATTTT
TGTAAACTGGAATTAAAAGGATAGTATTTTATCCACAATAGGC
CTGAAGATATTAATCCTGACCATTTGCTACTGTACATAAACAGT

```
GATGCCCTGCTCCAGGGAGACTTTGAGGTAATGATTTGGGAGGA

TTGCTGAAGGTCTCTCTTTCCCAGGGAGTCTCTGGGGCAGGCTG

CTTCAATCCCAGCTGAACTCGACTGAGGCTCTGTCTACCCCTTG

CTGGGTGGCAATGCCAATACTTCCGCTTTCTTTGATTCTATTTT

TATGTGTA                                                              1763
```

Precursors of sheep PACAP38 include a precursor which substantially corresponds to formula (8) or formula (9). Preferably, the precursor is represented by formula (8) or (9).

[Formula (8)]
Met Ala Lys Gly Leu Gly Gly Thr Pro Gly Gly

Gly Ala Asp Asp Asp Ser Glu Pro Leu Ser Lys

Arg His Ser Asp Gly Ile Phe Thr Asp Ser Tyr

Ser Arg Tyr Arg Lys Gln Met Ala Val Lys Lys

Tyr Leu Ala Ala Val Leu Gly Lys Arg Tyr Lys

Gln Arg Val Lys Asn Lys Gly Arg Arg Ile Pro

Tyr Leu

[Formula (9)]
Met Thr Met Cys Ser Gly Ala Arg Leu Ala Leu

Leu Val Tyr Gly Ile Leu Met His Ser Ser Val

Tyr Gly Ser Pro Ala Ala Ser Gly Leu Arg Phe

Pro Gly Ile Arg Pro Glu Asn Glu Ala Tyr Asp

Glu Asp Gly Asn Pro Gln Gln Asp Phe Tyr Asp

Ser Glu Pro Pro Gly Val Gly Ser Pro Ala Ser

Ala Leu Arg Asp Ala Tyr Ala Leu Tyr Tyr Pro

Ala Glu Glu Arg Asp Val Ala His Gly Ile Leu

Asp Lys Ala Tyr Arg Lys Val Leu Asp Gln Leu

Ser Ala Arg Arg Tyr Leu Gln Thr Leu Met Ala

Lys Gly Leu Gly Gly Thr Pro Gly Gly Gly Ala

Asp Asp Asp Ser Glu Pro Leu Ser Lys Arg His

Ser Asp Gly Ile Phe Thr Asp Ser Tyr Ser Arg

Tyr Arg Lys Gln Met Ala Val Lys Lys Tyr Leu

Ala Ala Val Leu Gly Lys Arg Tyr Lys Gln Arg

Val Lys Asn Lys Gly Arg Arg Ile Pro Tyr Leu

In the present invention, the DNAs containing the DNA segments coding for human PACAP38 include a DNA containing a nucleotide sequence which substantially corresponds to formula (4) or formula (5) and a DNA which substantially corresponds to a portion thereof. More preferably, the DNA is represented by formula (4) or (5) or a portion thereof.

[Formula (4)]
```
                                                    5' CAC TCG GAC GGG ATC
TTC ACG GAC AGC TAC AGC CGC TAC CGG AAA CAA ATG GCT GTC AAG
AAG TAC TTG GCG GCC GTC CTA GGG AAG AGG TAT AAA CAA AGG GTT
AAA AAC AAA GGA CGC CGA ATA GCT TAT TTG TAG CGA TGG GTT ACC
AGC TAC CCT GTG TAT AC 3'
      A ATG ACC ATG TGT AGC GGA GCG AGG CTG GCC CTG CTG GTC TAT
GGG ATA ATC ATG CAC AGC AGC GTC TAC AGC TCA CCT GCC GCC GCC
GGA CTC CGG TTC CCC GGG ATC AGG CCA GAG GAA GAG GCG TAC GGC
GAG GAC GGA AAC CCG CTG CCA GAC TTC GGT GGC TCG GAG CCG CCG
GGC GCA GGG AGC CCC GCC TCC GCG CCG CGC GCC GCC GCC GCC TGG
TAC CGC CCG GCC GGG AGA AGA GAT GTC GCC CAC GGG ATC CTT AAC
GAG GCC TAC CGC AAA GTG CTG GAC CAG CTG TCC GCC GGG AAG CAC
CTG CAG TCG CTC GTG GCC CGG GGC GTG GGT GGG AGC CTC GGC GGC
GGC GCG GGG GAC GAC GCG GAG CCG CTC TCC AAG CGC CAC TCG GAC
GGG ATC TTC ACG GAC AGC TAC AGC CGC TAC CGG AAA CAA ATG GCT
GTC AAG AAG TAC TTG GCG GCC GTC CTA GGG AAG AGG TAT AAA CAA
AGG GTT AAA AAC AAA GGA CGC CGA ATA GCT TAT TTG TAGCGATGGGT
```

-continued

```
TACCAGCTACCCTGTGTATACAGCCCTGACGCAATGAAAAGTCGTTTTCCAAACTGAC
TCAACAGTCATCGCTCGTGTGTTCTATCCAAACATGTATTTATGTAATGAAGTAAAGCC
ATTAAATGAATATTTTGATAATAATATTGTTTTTCTTTCTACAAAGCACTAGAGAATGC
ACAGATATACTTTGTGGACCAATTATTGATATATATTATAAATATATATAAAGAATATA
TATATATATATATATAAAGTATAGAGAGAAGTTCATACAAAGCGTGCACAAGGATTG
AAAATTCGCCCGAGCTGTTTATGTTTTTATAAAAATAAATAGAAAAGTAGACAATCATT
GTTTTGAATATTACTCCTATTTTTGTAAACTGGAATTAAAAGGATAGTATTTTATCCA
TGACAGGCCTGAAGATATTACTACTTACCATTTGCTACTGTACATAAACAATGATGCCC
TGCTCCAGGGAGATTTTGAGGTAAAGATATGGAGAATTGCTGAAGGGCATTCTTTCCCA
GTGAGTCTCTGGGGCAGGCTGCTTCAATCCCAGCCTAACTCAACTGGGCTCTGTCCCCC
TGGTTGGGTGGCAATTCCAATATTTCTGCTTTCTTTGATTCTCCTTTTATGTGTAGTTG
TCTCTCTTCAGACTCTCAGCCCAGAAGAAAATTCTCCTGATAAAACAACAGCTCGATCC
AAATTGTGCTTCTCCCCAGAATTCACGCCTCTCCCTAGGAGAAGAGTTGAGGAACTGTA
CAGAAAAGGGCGGCTTCGTTAGACCGCTCTCTTTTCTGTACTTCCTGAGTGGCCAGGGA
ATCTAATATCCCCAAATTAGGGCAATTGGAACAAAGTGAAGGACATAGAGGTATATTGG
AAGAGGCAGAGCCTGAGGTGGTAGGAGGAGGACCCTGGAAATGGACTGGTTTGAGATTG
CCCCAGGTCTGGGAAGCTGAGGGCAAATCCAGTCCCAGTGGTCCTGACTTTGGGCGCTG
GGTATTGGAAATGGATGCAAAGTACAATGTGTTTTCTCCAGTGCTGTCCATGCTTCTC
ATCTTGTGAAATGGCCAGGATCCTCTCCTTTGAAACCTGCTCTGTAGGAGCTACCCTTT
TCCTTTGTGGTTTTATGGAGACCTCTCCTTCCTACCCTCCTGCACTGTTTAAGTACTGT
TTACCATTTTTCATTCACTTCTCTTAAACTTGTGAATGCTTCTCACTTTTTTTTTTGT
TTGATGCAGGCACTTATTGTAAATTTTAGAAACCCCTCTGTAGCCACTAGTAAGTAATT
ATGCACTAAATATGAACCCTTTGTTTCTTGTTTATTGAGTTTGTAGGTAAAATGTATTT
TTCTACATTATTGCTTATTGCTTAGTAAAATTTATTTCATAAAA
```

Precursors of human PACAP38 include a precursor which substantially corresponds to formula (10) or formula (11). More preferably, the precursor is represented by formula (10) or (11).

[Formula (10)]
```
1                         7
Gly Gly Ser Leu Gly Gly Gly Ala Gly Asp Asp Ala Glu Pro Leu 19                              30
Ser Lys Arg His Ser Asp Gly Ile Phe Thr Asp Ser Tyr Ser Arg 45
Tyr Arg Lys Gln Met Ala Val Lys Lys Tyr Leu Ala Ala Val Leu 56          60
Gly Lys Arg Tyr Lys Gln Arg Val Lys Asn Lys Gly Arg Arg Ile 63
Ala Tyr Leu
```

[Formula 11]
```
    Met Thr Met Cys Ser Gly Ala Arg Leu Ala Leu Leu Val Tyr Gly Ile Ile Met His Ser Ser Val Tyr Ser Ser Pro Ala Ala Ala Gly Leu Arg Phe Pro Gly Ile Arg Pro Glu Glu Glu Ala Tyr Gly Gly Asp Gly Asn Pro Leu Pro Asp Phe Gly Gly Ser Glu Pro Pro Gly Ala Gly Ser Pro Ala Ser Ala Pro Arg Ala Ala Ala Ala Trp Tyr Arg Pro Ala Gly
```

Arg Arg Asp Val Ala His Gly Ile Leu Asn Glu Ala Tyr Arg Lys Val

Leu Asp Gln Leu Ser Ala Gly Lys His Leu Gln Ser Leu Val Ala Arg

Gly Val Gly Gly Ser Leu Gly Gly Gly Ala Gly Asp Asp Ala Glu Pro

Leu Ser Lys Arg <u>His Ser Asp Gly Ile Phe Thr Asp Ser Tyr Ser Arg</u>

<u>Tyr Arg Lys Gln Met Ala Val Lys Lys Tyr Leu Ala Ala Val Leu Gly</u>

<u>Lys Arg Tyr Lys Gln Arg Val Lys Asn Lys</u> Gly Arg Arg Ile Ala Tyr

Leu *

In the present invention, the DNAs containing the DNA segments coding for rat PACAP38 include a DNA containing a nucleotide sequence which substantially corresponds to formula (6) or formula (7) and a DNA which substantially corresponds to a portion thereof. More preferably, the DNA is represented by formula (6) or (7) or a portion thereof.

[Formula (6)]
```
                                    CAC TCG GAC GGC
ATC TTC ACA GAC AGC TAT AGC CGC TAC CGA AAA
CAA ATG GCT GTC AAG AAA TAC TTG GCG GCC GTG
CTA GGG AAA AGG TAT AAA CAG AGG GTT AAA AAC
AAA GGA CGC CGA ATA GCG TAC TTG TAG CGATGAG
TTGCCAGCTACCGTGTGTATAAAATGAAAAGTCGTTTTCCAAAT
TGACTGACCAGTCATCACTCATGTGTTCTTTCCAAACATGTATT
TATGTATCAAGTAAAGCCATTAAATGACTATTTTGATAATAATA
TTGTTTTTCTTTTTACGAAGCACTGGAGAATGCACAGATATACT
TTGTGGACCAATTATTGATATATATTATAAGTATATATTAAGAA
TATATATAGGTATAGCAGAGAGCAATTCATAAGCGTGCACAAAG
ATTGAAAATTCGCCTGAGCTGTTTATGTTTTATATAAAATGAA
TAGAGAAAATAGACAACCATTGTTTTGAATATTACTCCTATTTT
TGTAAACTGGAATTAAAGGATAGTATTTTTATCCACAACCGGCT
TGAAGATACCAATAATGGCCATTTGTACAAAAAAATGATGCCCT
GCTCCAGGAGAATTC
```

[Formula (7)]
```
GAATTCAGGACTCTCAAAGCTCCACAATGGCGCCCAGCTCTCTC
CTCAGCAACAGACTGAAGGCTTCGGCTAGTTTTGTGCGTCTACA
AAGCTTTGAGCGGAATTTTAGCTTCGGCAAACAAGTCCCCCCAG
CTCCTCCAGCTAATTCCCGCGACTTCTCTCCAGACACCAGCTCC
AGACAGTGACTGATGCCTCTCTGGTTGTGATTCCAGCGCAGAAA
CTCGAAGGAGCCCTTTGCCCGCCGTCCTATTTAGTCAACTCTTT
CCTAGCCGCGA ATG ACC ATG TGT AGC GGA GCA AGG
TTG GCC CTG TTG GTC TAC GGG ATA ATA ATG CAT
AAC AGC GTC TCC TGT TCA CCG GCC GCC GGA CTC
AGC TTC CCT GGG ATC AGA CCA GAA GAA GAG GCT
TAC GAT CAG GAC GGA AAC CCG CTG CAA GAC TTC
TAC GAC TGG GAC CCT CCG GGC GCA GGG AGC CCC
GCC TCC GCG CTG CGT GAC GCC TAC GCC CTT TAC
TAC CCA GCC GAC AGG AGA GAT GTC GCC CAC GAA
```

ATC CTT ACC GAA GCC TAC CGC AAA GTC TTG GAC
CAG CTG TCC GCC AGG AAG TAC CTG CAG TCC ATG
GTG GCC AGG GGC ATG GGC GAG AAC CTC GCC GCC
GCC GCG GTG GAC GAC CGG GCA CCC CTT ACC AAA
CGC CAC TCG GAC GGC ATC TTC ACA GAC AGC TAT
AGC CGC TAC CGA AAA CAA ATG GCT GTC AAG AAA
TAC TTG GCG GCC TGT CTA GGG AAA AGG TAT AAA
CAG AGG GTT AAA AAC AAA GGA CGC CGA ATA GCG
TAC TTG TAG CGATGAGTTGCCAGCTACCGTGTGTATAAAAT
GAAAAGTCGTTTTCCAAATTGACTGACCAGTCATCACTCATGTG
TTCTTTCCAAACATGTATTTATGTATCAAGTAAAGCCATTAAAT
GACTATTTTGATAATAATATTGTTTTCTTTTTACGAAGCACTG
GAGAATGCACAGATATACTTTGTGGACCAATTATTGATATATAT
TATAAGTATATATTAAGAATATATATAGGTATAGCAGAGAGCAA
TTCATAAGCGTGCACAAAGATTGAAAATTCGCCTGAGCTGTTTA
TGTTTTTATATAAAATGAATAGAGAAAATAGACAACCATTGTTT
TGAATATTACTCCTATTTTTGTAAACTGGAATTAAAGGATAGTA
TTTTTATCCACAACCGGCTTGAAGATACCAATAATGGCCATTTG
TACAAAAAAATGATGCCCTGCTCCAGGAGAATTC

Precursors of rat PACAP38 include a precursor which substantially corresponds to formula (12) or formula (13). Preferably, the precursor is represented by formula (12) or (13).

[Formula (12)]
Val Ala Arg Gly Met Gly Glu Asn Leu Ala Ala
Ala Ala Val Asp Asp Arg Ala Pro Leu Thr Lys
Arg His Ser Asp Gly Ile Phe Thr Asp Ser Tyr
Ser Arg Tyr Arg Lys Gln Met Ala Val Lys Lys
Tyr Leu Ala Ala Val Leu Gly Lys Arg Tyr Lys
Gln Arg Val Lys Asn Lys Gly Arg Arg Ile Ala
Tyr Leu ***

[Formula (13)]
Met Thr Met Cys Ser Gly Ala Arg Leu Ala Leu
Leu Val Tyr Gly Ile Ile Met His Asn Ser Val
Ser Cys Ser Pro Ala Ala Gly Leu Ser Phe Pro
Gly Ile Arg Pro Glu Glu Glu Ala Tyr Asp Gln
Asp Gly Asn Pro Leu Gln Asp Phe Tyr Asp Trp
Asp Pro Pro Gly Ala Gly Ser Pro Ala Ser Ala
Leu Arg Asp Ala Tyr Ala Leu Tyr Tyr Pro Ala
Asp Arg Arg Asp Val Ala His Glu Ile Leu Asn
Glu Ala Tyr Arg Lys Val Leu Asp Gln Leu Ser
Ala Arg Lys Tyr Leu Gln Ser Met Val Ala Arg
Gly Met Gly Glu Asn Leu Ala Ala Ala Ala Val
Asp Asp Arg Ala Pro Leu Thr Lys Arg His Ser
Asp Gly Ile Phe Thr Asp Ser Tyr Ser Arg Tyr
Arg Lys Gln Met Ala Val Lys Lys Tyr Leu Ala
Ala Val Leu Gly Lys Arg Tyr Lys Gln Arg Val
Lys Asn Lys Gly Arg Arg Ile Ala Tyr Leu ***

There is a common portion among sheep-, human- and rat- PACAP38 precursors, which is shown in formula (1'):

[Formula 1']
Lys Arg His Ser Asp Gly Ile Phe Thr Asp Ser Tyr Ser Arg
Tyr Arg Lys Gln Met Ala Val Lys Lys Tyr Leu Ala Ala Val
Leu Gly Lys Arg Tyr Lys Gln Arg Val Lys Asn Lys Gly Arg
Arg Ile The term "substantially corresponds" provides for conservative additions, deletions and or substitutions.

In the present invention, an expression vector having a DNA containing the nucleotide sequence coding for the precursor protein of PACAP38 or mature PA- CAP38 can be prepared, for example, by the following process:

(i) Messenger RNA (mRNA) is isolated from PACAP38-producing cells, (ii) Single stranded complementary DNA (cDNA) is synthesized from the mRNA, followed by synthesis of double stranded DNA, (iii) The complementary DNA is introduced into a phage or a plasmid, (iv) A host is transformed with the recombinant phage or plasmid thus obtained, (v) After cultivation of the transformant thus obtained, the plasmid or the phage containing the desired DNA is isolated from the transformant by an appropriate method such as hybridization with a DNA probe coding for a portion of PACAP38 or immunoassay using an anti-PACAP38 antibody, (vi) The desired cloned DNA is cut out from the recombinant DNA, and (vii) The cloned DNA or a portion thereof is ligated downstream from a promoter in the expression vector.

The mRNA coding for PACAP38 can be obtained from various PACAP38-producing cells such as sheep hypothalami, human hypothalami and testes, or rat hypothalami and testes.

Methods for preparing RNA from the PACAP38-producing cells include the guanidine thiocyanate method [J. M. Chirgwin et al., Bio-chemistry 18, 5294 (1979)].

Using the mRNA thus obtained as a template, cDNA is synthesized by use of reverse transcriptase, for example, in accordance with the method of H. Okayama et al. [Molecular and Cellular Biology 2, 161 (1982); ibid. 3, 280 (1983)]. The cDNA thus obtained is introduced into the plasmid.

The plasmids into which the cDNA is introduced include, for example, pBR322 [Gene 2, 95 (1977)], pBR325 [Gene 4, 121 (1978)], pUC12 [Gene 19, 259 (1982)] and pUC13 [Gene 19, 259 (1982)], each derived from Escherichia coli, and pUB110 derived from Bacillus subtilis [Biochemical and Biophysical Research Communication 112, 678 (1983)]. However, any other plasmid can be used as long as it is replicable and growable in the host. The phage vectors into which the cDNA is introduced include, for example, λgt11 [R. Young and R. Davis, Proc. Natl. Acad. Sci., U.S.A. 80, 1194 (1983)]. However, any other phage vector can be used as long as it is growable in the host.

Methods for introducing the cDNA into the plasmid include, for example, the method described in T. Maniatis et al., Molecular Cloning, Cold Spring Laboratory, p. 239 (1982). Methods for introducing the cDNA into the phage vector include, for example, the method of T. V. Hyunh et al. [DNA Cloning, A Practical Approach 1, 49 (1985)].

The plasmid thus obtained is introduced into the appropriate host cells such as Escherichia and Bacillus.

Examples of Escherichia described above include Escherichia coli K12DH1 [Proc. Natl. Acad. Sci. U.S.A. 60, 160 (1968)], M103 [Nucleic Acids Research 9, 309 (1981)], JA221 [Journal of Molecular Biology 120, 517, (1978)], HB101 [Journal of Molecular Biology 41, 459 (1969)] and C600 [Genetics 39, 440 (1954)].

Examples of Bacillus described above include Bacillus subtilis MI114 [Gene 24, 255 (1983)] and 207-21 [Journal of Biochemistry 95, 87 (1984)].

Methods for transforming the host with the plasmid include, for example, the calcium chloride method and the calcium chloride/rubidium chloride method described in T. Maniatis et al., Molecular Cloning, Cold Spring Harbor Laboratory, p.249 (1982).

When the phage vector is used, for example, the phage vector can be transduced into multiplied Escherichia coli, using the in vitro packaging method.

Each of sheep, rat and human cDNA libraries containing sheep, rat and human PACAP38 cDNAs, respectively, can be obtained by the methods described above and the like.

Methods for cloning each PACAP38 cDNA from each of the cDNA libraries include, for example, the method of Hyunh et al using phage vector λgt11 and an anti-PACAP38 antibody [DNA Cloning, A Practical Approach, p.49 (1985)] and the colony hybridization or plaque hybridization method using a oligonucleotide chemically synthesized on the basis of the amino acid sequence of PACAP38 as a probe [T. Maniatis et al., Molecular Cloning, Cold Spring Harbor Laboratory (1982)].

The PACAP38 cDNA thus cloned is subcloned to, for example, pBR322, pUC12, pUC13, pUC18, pUC19, pUC118, pUC119 or the like to obtain the sheep PACAP38 cDNA, if necessary.

The nucleotide sequence of the DNA thus obtained is determined by, for example, the Maxam-Gilbert method [A. M. Maxam and W. Gilbert, Proc. Natl. Acad. Sci., U.S.A. 74, 560 (1977)] or the dideoxy method [J. Messing et al., Nucleic Acids Research 9, 309 (1981)], and the existence of the PACAP38 cDNA is confirmed in comparison with the known amino acid sequence.

As described above, a DNA (sheep PACAP38 cDNA) [formula (2)] coding for a portion of the precursor protein of PACAP38 is obtained.

The restriction enzyme fragment map of the DNA coding for a portion of the precursor protein of sheep PACAP38 obtained in Example 1, which will hereinafter be described, is shown in FIG. 1. The nucleotide sequence of the cDNA determined by the dideoxy method and the amino acid sequence ascertained from that nucleotide sequence are shown in FIG. 21-2-2.

The DNA coding for a portion of the precursor protein of sheep PACAP38 cloned as described above can be used as it is, or cut out by digestion with a restriction enzyme if desired, according to the intended use.

The region intended to be expressed is cut out from the cloned DNA and ligated downstream from the promoter in a vehicle (vector) suitable for expression, whereby the expression vector can be obtained.

The DNA has ATG as a translation initiating codon at the 5'-terminus thereof and may have TAA, TGA or TAG as a translation terminating codon at the 3'-terminus. These translation initiating codon and translation terminating codons may be added by use of an appropriate synthetic DNA adaptor. Further, in order to express the DNA, the promoter is ligated to be upstream thereof.

The vectors include the above plasmids derived from Escherichia coli such as pBR322, pBR325, pUC12 and pUC13, the plasmids derived from Bacillus subtilis such as pUB110, pTP5 and pC194, plasmids derived from yeast such as pSH19 and pSH15, bacteriophages such as λphage, and animal viruses such as retroviruses and vaccinia viruses.

As the promoter used in the present invention, any promoter can be used as long as it is suitable for expression in the host cell used for the gene expression.

When the host cell used for transformation is Escherichia, it is preferable that a trp promoter, a lac promoter, a recA promoter, a λPL promoter, a lpp promoter or the like is used. When the host cell is Bacillus, it is preferable that a SPO1 promoter, a SPO2 promoter, a penP promoter or the like is used. When the host cell is yeast, it is preferred that a PHO5 promoter, a PGK promoter, a GAP promoter, an ADH promoter or the like is used. In particular, it is preferable that the host cell is Escherichia and the promoter is the trp promoter or the λPL promoter.

When the host is an animal cell, a SV40-derived promoter, a retrovirus promoter, a metallothionein promoter, a heat shock promoter or the like can be used.

The use of an enhancer is also effective for expression.

By using a vector containing the DNA coding for the precursor protein of PACAP38 or the mature peptide PACAP38 thus constructed, the transformant is prepared.

Examples of host cells include Escherichia, Bacillus, yeast and animal cells.

Specific examples of Escherichia and Bacillus include the strains described above.

Examples of the yeast described above include *Saccharomyces cerevisiae* AH22, AH22R⁻, NA87-11A and DKD-5D.

Examples of the animal cells include monkey cell COS-7, Vero, Chinese hamster cell (CHO), mouse L cell and human FL cell.

The transformation of Escherichia described above is conducted, for example, according to the method described in *Proc. Natl. Acad. Sci. U.S.A.*, 69, 2110 (1972); *Gene*, 17, 107 (1982) or the like.

The transformation of Bacillus is conducted, for example, according to the method described in *Molecular & General Genetics*, 168, 111 (1979) or the like.

The transformation of the yeast is carried out, for example, according to the method described in *Proc. Natl. Acad. Sci. U.S.A.*, 75, 1929 (1978).

The transformation of animal cells is carried out, for example, according to the method described in *Virology*, 52, 456 (1973).

Thus, the transformant transformed with the expression vector containing the DNA coding for a portion of the precursor protein of PACAP38 or the mature peptide (PACAP38) is obtained.

When the transformant wherein the host cell is Escherichia or Bacillus is cultivated, a liquid medium is particularly suitable as a medium for cultivation. Carbon sources, nitrogen sources, inorganic compounds and others necessary for growth of the transformants are contained therein. The carbon sources include, for example, glucose, dextrin, soluble starch and sucrose. The nitrogen sources include inorganic or organic materials such as ammonium salts, nitrates, corn steep liquor, peptone, casein, meat extracts, soybean meal and potato extract solution. The inorganic compounds include, for example, calcium chloride, sodium dihydrogenphosphate and magnesium chloride. Further, yeast, vitamins, growth promoting factors and so on may be added thereto.

The pH of the medium is preferably about 5 to 8.

As the medium for cultivation of Escherichia, it is preferable to use, for example, M9 medium containing glucose and Casamino Acids (Miller, *Journal of Experiments in Molecular Genetics*, 431–433, Cold Spring Harbor Laboratory, New York, 1972). In order to make the promoter act efficiently, a drug such as 3-indolylacrylic acid may be added thereto, if necessary.

When the host cell is Escherichia, the cultivation is usually carried out at about 15° to 43° C. for about 3 to 24 hours, with aeration or agitation if necessary.

When the host cell is Bacillus, the cultivation is usually carried out at about 30° to 40° C. for about 6 to 24 hours, with aeration or agitation if necessary.

When the yeast transformants are cultivated, there is used, for example, Burkholder minimum medium [K. L. Bostian et al., *Proc. Natl. Acad. Sci. U.S.A.*, 77, 4505 (1980)] as the medium. The pH of the medium is preferably adjusted to about 5 to 8. The cultivation is usually carried out at about 20° to 35° C. for about 24 to 72 hours, with aeration or agitation if necessary.

When the animal cell transformants are cultivated, there can be used as the medium, for example, MEM medium containing about 5 to 20% fetal calf serum [*Science*, 122, 501 (1952)], DMEM medium [*Viroloqy*, 8, 396 (1959)], RPMI1640 medium [*The Journal of the American Medical Association*, 199, 519 (1967)] and 199 medium [*Proceeding of the Society for the Biological Medicine*, 73, 1 (1950)]. The pH is preferably about 6 to 8. The cultivation is usually carried out at about 30° to 40° C. for about 15 to 60 hours, with aeration or agitation if necessary.

A portion of the precursor protein of PACAP38 or the mature peptide (PACAP38) can be isolated and purified from the culture described above, for example, by the following method.

When a portion of the precursor protein of PACAP38 or the mature peptide (PACAP38) is extracted from the cultivated cells, the cells are collected by a known method after cultivation. Then, the collected cells are suspended in an appropriate buffer solution and disrupted by ultrasonic treatment, lysozyme and/or freeze-thawing. Thereafter, a crude extracted solution of a portion of the precursor protein of sheep PACAP38 or the mature peptide is obtained by centrifugation or filtration. The buffer may contain a protein denaturant such as urea or guanidine hydrochloride, or a surface-active agent such as Triton X-100.

When a portion of the precursor protein of PACAP38 or the mature peptide is secreted in the culture solution, the supernatant is separated from the cells by a known method per se after the conclusion of cultivation, and then collected. The separation and purification of a portion of the precursor protein of sheep PACAP38 or the mature peptide contained in the supernatant or the extracted solution thus obtained can be performed by an appropriate combination of known separating and purifying methods per se. These known separating and purifying methods include methods utilizing solubility such as salt precipitation and solvent precipitation, methods mainly utilizing a difference in molecular weight such as dialysis, ultrafiltration, gel filtration and SDS-polyacrylamide gel electrophoresis, methods utilizing a difference in electric charge such as ion-exchange column chromatography, methods utilizing specific affinity such as affinity chromatography, methods utilizing a difference in hydrophobicity such as reverse-phase high performance liquid chromatography and methods utilizing a difference in isoelectric point such as isoelectro focusing electrophoresis.

The activity of a portion of the PACAP38 precursor protein or the mature peptide thus formed can be measured by an enzyme immunoassay using a specific antibody. If the products have the vasoconstrictive activity, the activity may be measured as an index.

The cells transfected or transformed with the DNA of the present invention can produce a large amount of the precursor protein of PACAP38 or the PACAP38 peptide. The DNA of the present invention is therefore applied to experimental animals to understand its action, particularly brain functions, more particularly brain functions due to hormones. Further, the information thus obtained provides information which serves to elucidate human brain functions.

Furthermore, PACAP38 has the rising activity of cAMP. Hence, information about growth and maintenance of rat and human brain nerves can be obtained thereby, and PACAP38 can also be utilized as therapeutic agents for various neuropathy.

There were hereinbefore described in detail the cloning of the cDNAs coding for sheep, human and rat PACAP38, the preparation of expression vectors of portions of the sheep, human and rat PACAP38 precursors and mature peptides, the preparation of transformants thereby, the production of portions of PACAP38 precursor proteins and mature peptides by use of the transformants, and the utility thereof.

When nucleotides, amino acids and so on are indicated by abbreviations in the specification and drawings, the abbreviations adopted by IUPAC-IUB Commission on Biochemical Nomenclature or commonly used in the art are employed. For example, the following abbreviations are used. When an optical isomer is capable of existing with respect to the amino acids, the L-form is represented unless otherwise specified.

DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetraacetic acid
SDS: Sodium dodecyl sulfate
BHA: Benzhydrylamine
Cl-Z: 2-Chloro-benzyloxycarbonyl
Br-Z: 2-Bromo-benzyloxycarbonyl
Bzl: Benzyl
OBzl: Benzyl ester
HOBt: 1-Benzotriazole
DCC: N,N'-Dichlorohexylcarbodiimide
Gly or G: Glycine
Ala or A: Alanine
Val or V: Valine
Leu or L: Leucine
Ile or I: Isoleucine
Ser or S: Serine
Thr or T: Threonine
Cys or C: Cysteine
Met or M: Methionine
Glu or E: Glutamic acid
Asp or D: Aspartic acid
Lys or K: Lysine
Arg or R: Arginine
His or H: Histidine
Phe or F: Phenylalanine
Tyr or V: Tyrosine
Trp or W: Tryptophan
Pro or P: Proline
Asn or N: Asparagine
Gln or Q: Glutamine With respect to the PACAP38 precursor proteins or the mature peptides of the present invention, a portion of the amino acid sequence may be modified, so long as it does not adversely affect biological properties, namely there may be addition, elimination or substitution with other amino acid.

The present invention will be described in more detail with the following Reference Examples and Examples. It is understood of course that these Reference Examples and Examples are not intended to limit the scope of the invention.

Transformant *Escherichia coli* DH5α/pOH38P7 obtained in Example 2 described below was deposited with the Fermentation Research Institute, Agency of Industrial Science and Technology, Ministry of International Trade and Industry, Japan (FRI) with the accession number FERM BP-2484 on Jun. 19, 1989. This microorganism was also deposited in the Institute for Fermentation, Osaka, Japan (IFO) with the accession number IFO 14884 on June 15, 1989.

Transformant *Escherichia coli* DH5α/pHT38P8 obtained in Example 3 described below was deposited with the Fermentation Research Institute, Agency of Industrial Science and Technology, Ministry of International Trade and Industry, Japan (FRI) with the accession number FERM BP-2622 on, Oct. 4, 1989. This microorganism was also deposited in the Institute for Fermentation, Osaka, Japan (IFO) with the accession number IFO 14953 on Sep. 28, 1989.

Transformant *Escherichia coli* JM109/pRB38P21 obtained in Example 4 described below was deposited with the Fermentation Research Institute, Agency of Industrial Science and Technology, Ministry of International Trade and Industry, Japan (FRI) with the accession number FERM BP-2762 on Feb. 19, 1990.

REFERENCE EXAMPLE 1

The amino acid sequence of sheep PACAP38 was identical to that of human PACAP38. When PACAP38 (Nat.38p) purified from sheep hypothalami and synthesized PACAP38 (Syn.38p) were allowed to act on rat pituicytes in vitro, an increase in adenylate cyclase activity was observed. The minimum effective amount was 10M, and it was shown that the activity increased with increasing concentration.

Further, similar activity was also observed for synthesized 27-NH2 [the amino acids situated in the 132nd to 158th positions in FIG. 2-1-2-2, the 1st to 27th positions of mature PACAP38, Syn.27p-NH2 in the following table. The sequence is shown in formula (1")].

[Formula 1"]
His Ser Asp Gly Ile Phe Thr Asp Ser Tyr Ser Arg Tyr Arg

-continued

Lys Gln Met Ala Val Lys Lys Tyr Leu Ala Ala Val Leu

In contrast, the corresponding activity could not be observed for a synthesized porcine VIP (vasoactive intestinal polypeptide).

| | cAMP p mol/ml (M ± SEM) |
|---|---|
| Control (Blank) | 1.55 ± 0.15 |
| Syn.pVIP $10^{-12}$ M | 1.35 ± 0.05 |
| Syn.pVIP $10^{-11}$ M | 1.40 ± 0.00 |
| Syn.pVIP $10^{-10}$ M | 1.45 ± 0.15 |
| Syn.pVIP $10^{-9}$ M | 1.75 ± 0.05 |
| Syn.pVIP $10^{-8}$ M | 2.55 ± 0.25 |
| Syn.pVIP $10^{-7}$ M | 3.30 ± 0.20 |
| Syn.27p-NH$_2$ $10^{-12}$ M | 2.05 ± 0.15 |
| Syn.27p-NH$_2$ $10^{-11}$ M | 2.55 ± 0.15 |
| Syn.27p-NH$_2$ $10^{-10}$ M | 4.00 ± 0.20 |
| Syn.27p-NH$_2$ $10^{-9}$ M | 7.90 ± 0.30 |
| Syn.27p-NH$_2$ $10^{-8}$ M | 9.20 ± 0.00 |
| Syn.27p-NH$_2$ $10^{-7}$ M | 9.20 ± 0.20 |
| Syn.38p $10^{-12}$ M | 2.15 ± 0.05 |
| Syn.38p $10^{-11}$ M | 3.05 ± 0.35 |
| Syn.38p $10^{-10}$ M | 4.60 ± 0.20 |
| Syn.38p $10^{-9}$ M | 6.20 ± 0.10 |
| Syn.38p $10^{-8}$ M | 8.60 ± 0.20 |
| Syn.38p $10^{-7}$ M | 8.70 ± 0.20 |
| Nat.38p $10^{-12}$ M | 1.50 ± 0.10 |
| Nat.38p $10^{-11}$ M | 1.75 ± 0.05 |
| Nat.38p $10^{-10}$ M | 2.60 ± 0.10 |
| Nat.38p $10^{-9}$ M | 4.60 ± 0.00 |
| Nat.38p $10^{-8}$ M | 8.05 ± 0.35 |
| Control (Blank) | 1.35 ± 0.05 |

REFERENCE EXAMPLE 2

The materials used in Reference Example 1 were similarly allowed to act on rat pituicytes. As a result, the releasing activity of prolactin (PRL), ACTH and GH was confirmed therein.

EXAMPLE 1

Preparation of DNA Probe Coding for a Portion of Sheep PACAP38

A messenger RNA sequence, was deduced from the amino acid sequence composed of the 1st to the 27th residues of sheep PACAP38, His Ser Asp Gly Ile Phe Thr Asp Ser Tyr Ser Arg Tyr Arg Lys Gln Met Ala Val Lys Lys Tyr Leu Ala Ala Val Leu, and a DNA probe having the following sequence was chemically synthesized.

5'-CACTCTGATGGAATCTTCACAGATAGC-TACAGCCGCTATAGAAAGCAAATG-3' and
3'-TCGGCGATATCTTTCGTTTACC-GACACTTCTTTATGAACCGGCGGCAA-GAT-5'

The 5'-terminus of this DNA probe was phosphorylated with $^{32}$P by using T4 polynucleotide kinase. The phosphorylated DNA probe was used for screening of the cDNA library.

EXAMPLE 2

Isolation of Sheep PACAP38 Precursor cDNA and Determination of Nucleotide Sequence Thereof

*Escherichia coli* Y1090 was infected with the above sheep hypothalamus cDNA library (Clontech Laboratories, Inc.) and plated to cause phage plaques to appear. A portion of plague DNA was transferred to a nitrocellulose film according to the method of W. Benton and R. Davis [*Science* 196, 180–182 (1977)] and hybridized with the DNA probe labeled with $^{32}$P in Example 1. Hybridization was carried out in the absence of formaldehyde at 60° C. Each of 5 clones positive to the hybridization was isolated. Then, a cDNA portion of λOH38P7, which was one of the clones described above, was cut out with EcoRI and recloned into the EcoRI site of plasmid pUC18 to prepare plasmid pOH38P7. By transforming *Escherichia coli* DH5α with this plasmid, transformant *Escherichia coli* DH5α/-pOH38P7 was obtained. The cDNA portion included in this plasmid was 1.8 Kbp, and the simplified restriction enzyme map thereof is shown in FIG. 1. In the figure, ² shows a mature sheep PACAP38 code region. The nucleotide sequence of this cDNA portion was determined by the method of Sanger [*Proc. Natl. Acad. Sci. U.S.A.* 74, 5463–5467 (1977)]. This nucleotide sequence and a portion of the amino acid sequence of the sheep PACAP38 precursor presumed therefrom are shown in FIG. 2-1-2-2. The region surrounded by □ ³ shows the mature peptide portion of sheep PACAP38.

EXAMPLE 3

Isolation of Human PACAP38 Precursor cDNA and Determination of Nucleotide Sequence Thereof

Figure 3:
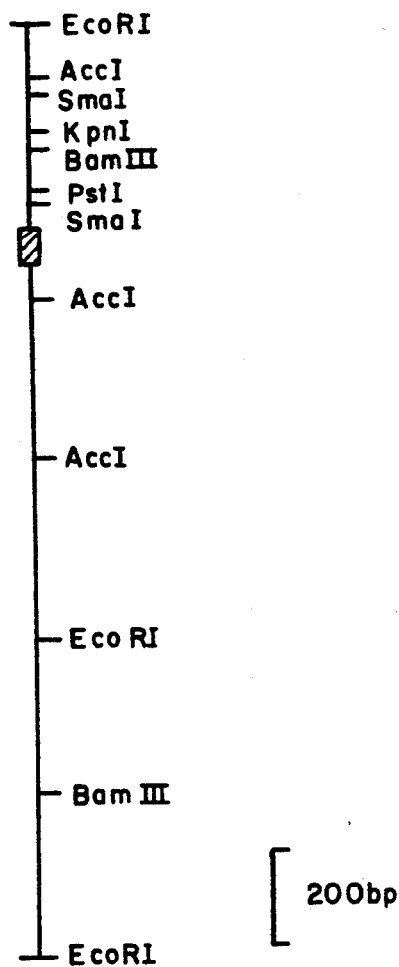
FIG. 3 is a simplified restriction enzyme map of the cDNA coding for a portion of a human PACAP38 precursor.

*Escherichia coli* Y1090 was infected with the above testis cDNA library (Clontech Laboratories, Inc.) and plated to cause phage plaques to appear. A portion of plaque DNA was transferred to a nitrocellulose film according to the method of W. Benton and R. Davis [*Science* 196, 180–182 (1977)] and hybridized with the DNA probe labeled with $^{32}$P in Example 1. The hybridization was carried out in the absence of formaldehyde at 60° C. Each of 5 clones positive to hybridization was isolated. Then, a cDNA portion of HT38P8 which was one of the clones described above was cut out with EcoRI and recloned into the EcoRI site of plasmid pUC18 to prepare plasmid pHT38P8. By transforming *Escherichia coli* DH5α with this plasmid, transformant *Escherichia coli* DH5α/pHT38P8 was obtained. The cDNA portion included in this plasmid was 2.3 Kbp, and the simplified restriction enzyme map thereof is shown in FIG. 3. In the figure, ² shows a mature human PACAP38 code region. The nucleotide sequence of this cDNA portion was determined by the method of Sanger [*Proc. Natl. Acad. Sci. U.S.A.* 74, 5463–5467 (1977)]. This nucleotide sequence and a portion of the amino acid sequence of the human PACAP38 precursor deduced therefrom are shown in FIG. 4-1-4-2. The region surrounded by ⁴ shows the mature peptide portion of human PACAP38.

EXAMPLE 4

Isolation of Rat PACAP38 Precursor cDNA and Determination of Nucleotide Sequence Thereof

Figure 5:
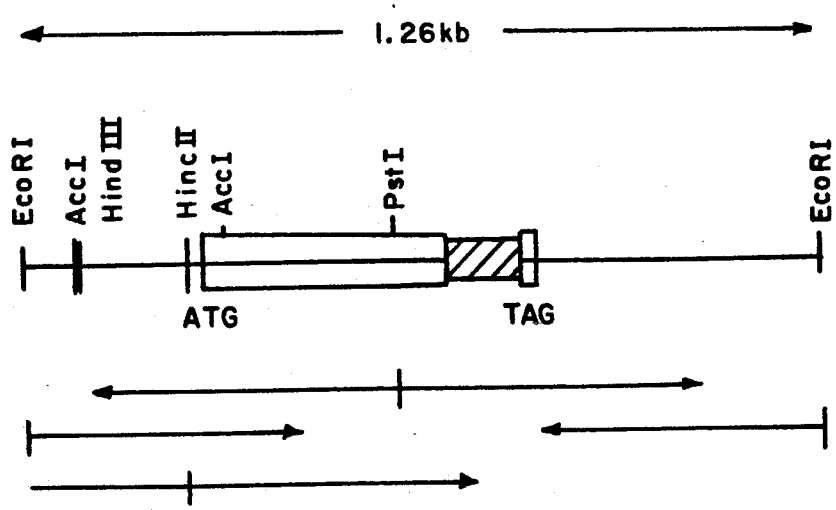
FIG. 5 is a simplified restriction enzyme map of the cDNA coding for a portion of a rat PACAP38 precursor.

*Escherichia coli* Y1090 was infected with the above testis cDNA library (Clontech Laboratories, Inc.) and plated to cause phage plaques to appear. A portion of plaque DNA was transferred to a nitrocellulose film according to the method of W. Benton and R. Davis [*Science* 196, 180–182 (1977)] and hybridized with the DNA probe labeled with $^{32}$P in Example 1. The hybridization was carried out in the absence of formaldehyde at 60° C. Each of 4 clones positive to hybridization was isolated. Then, a cDNA portion of RB38P68 which was one of the clones described above was cut out with EcoRI and recloned into the EcoRI site of plasmid pUC18 to prepare plasmid pRB38P21. By transforming *Escherichia coli* JM109 with this plasmid, transformant *Escherichia coli* JM109/pRB38P21 was obtained. The cDNA portion included in this plasmid was 1.2 Kbp, and the simplified restriction enzyme map thereof is shown in FIG. 5. In the figure, ² shows a mature rat PACAP38 code region. The nucleotide sequence of this cDNA portion was determined by the method of Sanger [*Proc. Natl. Acad. Sci. U.S.A.* 74, 5463–5467 (1977)]. This nucleotide sequence and a portion of the amino acid sequence of the rat PACAP38 precursor deduced therefrom are shown in FIG. 6-1-6-2. The region surrounded by ⁴ shows the mature peptide portion of rat PACAP38.

EXAMPLE 5

Synthesis of PACAP38 NH₂

PACAP38 NH₂ was synthesized by using 1.04 g (0.5 mmole) of a commercially available p-methyl BHA resin (Applied Biosystems Inc.) and a peptide synthesizer (Model 430A, Applied Biosystems Inc.). 10 A starting amino acid, Boc-Lys(Cl-Z), was activated with HOBt/DCC and then condensed to the resin. Thereafter, the Boc group on the resin was treated with 50% trifluoroacetic acid/methylene chloride to deprotect the amino group. To this free amino group, the following protected amino acids activated with HOBt/DCC were condensed in turn according to the amino acid sequence of PACAP38:

Boc—Asn, Boc—Lys(Cl—Z), Boc—Val, Boc—Arg(Tos),
Boc—Gln, Boc—Tyr(Br—Z), Boc—Gly, Boc—Leu, Boc—Ala,
Boc—Met, Boc—Ser(Bzl), Boc—Asp(OBzl), Boc—Thr(Bzl),
Boc—Phe, Boc—Ile, and Boc—His(Tos)

After the completion of each reaction, the residual amino groups were acetylated with acetic anhydride to obtain 2.42 g of a protected PACAP38 NH₂ resin.

0.51 g of the resulting protected PACAP38 NH₂ resin was treated with 5 ml of hydrogen fluoride in the presence of 0.6 g of p-cresol at 0° C. for 60 minutes, followed by removal of excess hydrogen fluoride by distillation under reduced pressure. The residue was washed twice with 5 ml of ethyl ether, and then extracted with 6 ml of 50% aqueous acetic acid. The insoluble material was removed by filtration and washed with 5 ml of 50% aqueous acetic acid. The filtrate and the washings were combined, and the combined solution was concentrated to 2 to 3 ml. The concentrated solution was applied on a Sephadex LH-20 column (2×90 cm) for elution with 50% acetic acid. The main fractions were collected, followed by removal by distillation under reduced pressure. Then, the residue was dissolved in 100 ml of 0.1% aqueous trifluoroacetic acid. The resulting solution was subjected to a YMC-ODS AM120 S-50 resin column (1.6×7 cm) and eluted by a linear gradient of 0.1% aqueous trifluoroacetic acid and 50% acetonitrile containing 0.1% trifluoroacetic acid.

The main fractions were combined, followed by lyophilization. Thus, 60 mg of white powder was obtained. This powder was dissolved in 20 ml of 0.05M aqueous ammonium acetate. The resulting solution was subjected to a CM-Cellulofine resin column (1×6 cm) and eluted by a linear gradient of from 0.05M to 1M ammonium acetate. The main fractions were combined.

The combined solution was subjected to a YMC-ODS column (2.6×7 cm) again and eluted by a linear gradient of from 0% to 40% aqueous acetonitrile containing 0.1% trifluoroacetic acid. The fractions of 28% to 30% acetonitrile were collected, followed by lyophilization. Thus, 21.6 mg of white powder was obtained.

Anal. for amino acids: Asp 2.90(3), Thr 0.84(1), Ser 2.10(3), Glu 2.21(2), Gly 2.00(2), Ala 3.29(3), Val 3.19(3), Met 1.01(1), Ile 0.87(1), Leu 2.19(2), Tyr 3.93(4), Phe 0.92(1), Lys 7.18(7), His 0.96(1), Arg 4.19(4).

(M+H)⁺ by mass spectrography (SIMS): 4530.
HPLC elution time: 19.6 minutes.
Column conditions
Column: YMC-ODS (AM-301, S-5 120A)
Eluent:
    A (0.1%aqueous trifluoroacetic acid)
    B (acetonitrile containing 0.1% trifluoroacetic acid)
A linear gradient elution from the eluent A to the eluent B for 50 minutes
Flow rate: 1.0 ml/minute

EXAMPLE 6

Synthesis of PACAP27 NH2

PACAP27 NH₂ was synthesized by using 1.04 g (0.5 mmole) of a commercially available p-methyl BHA resin (Applied Biosystems Inc.) and a peptide synthesizer (Model 430A, Applied Biosystems Inc.).

A starting amino acid, Boc-Leu, was activated with HOBt/DCC and then condensed to the resin. Thereafter, the Boc group on the resin was treated with 50% trifluoroacetic acid/methylene chloride to deprotect the amino group. To this free amino group, the following protected amino acids activated with HOBt/DCC were condensed in turn according to the amino acid sequence of PACAP38 (1-27):

Boc—Val, Boc—Ala, Boc—Leu, Boc—Tyr(Br—Z),
Boc—Lys(Cl—Z), Boc—Met, Boc—Gln, Boc—Arg(Tos),
Boc—Ser(Bzl), Boc—Asp(OBzl), Boc—Thr(Bzl), Boc—Phe,
Boc—Ile, and Boc—His(Tos)

After the completion of each reaction, the residual amino groups were acetylated with acetic anhydride to obtain 2.31 g of a protected PACAP27 NH₂ resin.

0.50 g of the resulting protected PACAP27 NH₂ resin was treated with 5 ml of hydrogen fluoride in the presence of 0.6 g of p-cresol at 0° C. for 60 minutes, followed by removal of excess hydrogen fluoride by distillation under reduced pressure. The residue was washed twice with 5 ml of ethyl ether, and then extracted with 6 ml of 50% aqueous acetic acid. The insoluble material was removed by filtration and washed with 5 ml of 50% aqueous acetic acid. The filtrate and the washings were combined, and the combined solution was concentrated to 2 to 3 ml. The concentrated solution was applied on a Sephadex LH-20 column (2×90 cm) for elution with 50% acetic acid. The main fractions were collected, followed by lyophilization to obtain 129 mg of white powder. This powder was dissolved in 5 ml of 0.1% aqueous trifluoroacetic acid. The resulting solution was subjected to a TSK-GEL (ODS-120T) column (21.5×300 mm) and eluted with 27% acetonitrile containing 0.1% aqueous trifluoroacetic acid.

The main fractions were collected, followed by lyophilization. Thus, 17.2 mg of white powder was obtained. Anal. for amino acids:

Asp 1.99(2), Thr 0.98(1), Ser 2.76(3), Glu 1.25(1), Gly 1.05(1), Ala 3.0 (3), Val 1.56(2), Met 0.78(1), Ile 0.72(1), Leu 1.88(2), Tyr 2.22(3), Phe 0.75(1), Lys 2.73(3), His 1.51(1), Arg 1.94(2).

(M+H)+ by mass spectrography (SIMS): 3145.
HPLS elution time: 21.2 minutes.

Column conditions
Column: YMC-ODS (AM-301, S-5 120A)
Eluent:
A (0.1% aqueous trifluoroacetic acid)
B (acetonitrile containing 0.1% trifluoroacetic acid)
A linear gradient elution from the eluent A to the eluent B for 50 minutes
Flow rate: 1.0 ml/minute

EXAMPLE 7

Using male Wistar rats having a body weight of 350 g under nembutal anesthesia, the hypotensive activity was measured. The results are shown in Table 1.

TABLE 1

| Compound | Dosage (n mole/kg) | | |
|---|---|---|---|
| | 0.3 | 1.0 | 3.0 |
| PACAP38 NH$_2$ | 3.2 ± 1.9 (n = 6) | 17.4 ± 2.4 (n = 6) | 29.8 ± 3.6 (n = 6) |
| PACAP27 NH$_2$ | 14.5 ± 3.1 (n = 5) | 51.9 ± 9.6 (n = 5) | 4.1 (n = 1) |

Unit: mm Hg

The following references, which are referred to for their disclosures at various points in this application, are incorporated herein by reference.

Japanese Patent Application Nos. 1-155791/1990, 1-284771/1990 and 1-259924/1990,
Biochemistry 18, 5294 (1979),
Molecular and Cellular Biology 2, 161 (1982),
Molecular and Cellular Biology 3, 280 (1983),
Gene 2, 95 (1977),
Gene 4, 121,
Gene 19, 259 (1982),
Biochemical and Biophysical Research Communication 112, 678 (1983),
Proc. Natl. Acad. Sci., U.S.A. 80, 1194 (1983),
Molecular Cloning, Cold Spring Laboratory, p. 239 (1982),
DNA Cloning, A Practical Approach 1, 49 (1985),
Proc. Natl. Acad Sci. U.S.A. 60, 160 (1968),
Nucleic Acids Research 9, 309 (1981)
Journal of Molecular Biology 120, 517, (1978),
Journal of Molecular Biology 41, 459 (1969),
Genetics 39, 440 (1954),
Gene 24, 255 (1983),
Journal of Biochemistry 95, 87 (1984),
Proc. Natl. Acad. Sci., U.S.A. 74, 560 (1977),
Proc. Natl. Acad. Sci. U.S.A., 69, 2110 (1972),
Gene, 17, 107 (1982),
Molecular & General Genetics, 168, 111 (1979),
Proc. Natl. Acad. Sci. U.S.A., 75, 1929 (1978),
Virology, 52, 456 (1973),
Journal of Experiments in Molecular Genetics, 431-433, Cold Spring Harbor Laboratory, New York, 1972,
Proc. Natl. Acad. Sci. U.S.A., 77, 4505 (1980),
Science, 122, 501 (1952),
Virology, 8, 396 (1959),
The Journal of the American Medical Association, 199, 519 (1967),
Proceeding of the Society for the Biological Medicine, 73, 1 (1950),
Science 196, 180-182 (1977),
Proc. Natl. Acad. Sci. U.S.A. 74, 5463-5467 (1977),

What is claimed is:

1. An isolated DNA comprising a DNA segment coding for PACAP38.

2. An isolated DNA comprising a DNA segment coding for a polypeptide having the following formula:

| His | Ser | Asp | Gly | Ile | Phe | Thr | Asp | Ser | Tyr | Ser | Arg | Tyr | Arg |
|---|---|---|---|---|---|---|---|---|---|---|---|---|---|
| Lys | Gln | Met | Ala | Val | Lys | Lys | Tyr | Leu | Ala | Ala | Val | Leu | Gly |
| Lys | Arg | Tyr | Lys | Gln | Arg | Val | Lys | Asn | Lys | | | | |

3. An isolated DNA as claimed in claim 1, in which the DNA segment coding for PACAP38 is a DNA segment coding for sheep PACAP38, said DNA segment comprising a nucleotide sequence having the following formula or a portion thereof which codes for a functional PACAP38:

| 5' | CAC | TCG | GAC | GGC | ATC | TTC | ACT | GAC | AGC | TAC |
|---|---|---|---|---|---|---|---|---|---|---|
| | AGC | CGC | TAC | CGG | AAG | CAA | ATG | GCT | GTT | AAG | AAA |
| | TAC | TTG | GCG | GCT | GTC | CTA | GGG | AAA | AGG | TAT | AAA |
| | CAA | AGG | GTT | AAG | AAC | AAA | GGA | CGG | CGA | ATA | CCG |
| | TAC | TTG | TAG | CGA | CGA | GTT | ACC | AGC | TAT | CCT |

***

4. An isolated DNA as claimed in claim 3, in which the DNA segment coding for sheep PACAP38 comprise a nucleotide sequence having the following formula or a portion thereof which codes for a functional PACAP38:

```
CTGCTAACTGCCCAGATAAATAGGAGCAGAGGGCTGGTCAC
CTCTGTAATAACCACCGGCAGCAGTAGAAGAAACCGCAGCTTCA
GAAGCAGCCAGAGAGACTTCTGAGCAGCGAAGGCGCTGCCTGCT
CGAGCTGCCTGGCCGGGCGGCTGCCCCAGACGCCGACTTCGCCG
AGGCCCTCTCTCTCTCTCTCTCTCTCTCTCTCTCTCTCTCTCTC
TCTCTCTGCTTCTTTCCTTATCACTCCTTTCTTCTCAGTGGACT
TCAGGCCACTTTGTCTCCCACCCCCACTCAGCTCGTCGCCTCCT
CCGTCTTCCTTCTCCATCTCTCCTCTCGCCCCCCTTCTCTCAGT
GTCACGCTCCGTCCTAGTTCCGAGCGTCGTCAAACTTTTGAACA
```

-continued
```
GAATAACAGGACTCAGCAAACAAGTCCTCCAGCTCCTCCCGCGG
CTCCGGCTCGTTCCTGCGGCTCCTGCTCAGACACTAACGCCAGA
CGGCGATGCCTCTTGGGTTGTGACTACAGCGCACAAACTTGGAG
AAGCTCTTTGCCCGCCGTCCTACTTGGCAGCAAATCCTCTCCTG
GCAGCGA ATG  ACC  ATG  TGT  AGC  GGA  GCG  AGG  CTG
GCC  CTG  CTC  GTT  TAC  GGG  ATA  CTG  ATG  CAC  AGC
AGC  GTC  TAC  GGC  TCA  CCT  GCC  GTC  TCC  GGA  CTC
CGG  TTC  CCG  GGG  ATC  AGG  CCG  GAG  AAC  GAG  GCG
TAC  GAC  GAG  GAC  GGA  AAC  CCG  CAG  CAG  GAC  TTC
TAC  GAC  TCG  GAG  CCG  CCA  GGC  GTG  GGG  AGC  CCC
GCC  TCC  GCG  CTG  CGC  GAT  GCC  TAC  GCG  CTC  TAC
TAC  CCG  GCG  GAG  GAA  AGA  GAT  GTC  GCC  CAC  GGG
ATC  CTT  GAT  AAG  GCC  TAC  CGC  AAA  GTG  CTG  GAC
CAG  CTG  TCC  GCC  AGG  AGA  TAC  CTG  CAG  ACG  CTC
ATG  GCC  AAG  GGC  TTG  GGT  GGG  ACC  CCG  GGC  GGC
GGC  GCG  GAC  GAC  GAC  TCG  GAG  CCG  CTC  TCC  AAG
CGC  CAC  TCG  GAC  GGC  ATC  TTC  ACT  GAC  AGC  TAC
AGC  CGC  TAC  CGG  AAG  CAA  ATG  GCT  GTT  AAG  AAA
TAC  TTG  GCG  GCT  GTC  CTA  GGG  AAA  AGG  TAT  AAA
CAA  AGG  GTT  AAG  AAC  AAA  GGA  CGG  CGA  ATA  CCG
TAC  TTG  TAG  CGACGAGTTACCAGCTATCCTGTGTATACAGC
CCTGACACAATGAGAAGTCGTTTTTCCCAACTGACTGAACTGTC
ATCGCTGCTGTGTTCTGTCCCACATGTATTTATGTATGAAGTCA
AGCCATTAAATGAATATTTTGATAATAATATTGTTTTTTCTTTTT
ACGAAGCACTGGAGAATGCACAGATATACTTTGTGGACCAATTA
TTGATATTGACATATATATTACGAATATATAAAGAGTATATATA
TATATATATAAGTATAATAGAGAGCCGTTCATACAGTGTGCACA
AGGACTGAAGATTCGCCTGAGCTGTTTGTTTTTATATAAAATAA
ATAGAAAAATAGACAATCATTGTTTTGAATATTACTCCTATTTT
TGTAAACTGGAATTAAAAGGATAGTATTTTTATCCACAATAGGC
CTGAAGATATTAATCCTGACCATTTGCTACTGTACATAAACAGT
GATGCCCTGCTCCAGGGAGACTTTGAGGTAATGATTTGGGAGGA
TTGCTGAAGGTCTCTCTTTCCCAGGGAGTCTCTGGGGCAGGCTG
CTTCAATCCCAGCTGAACTCGACTGAGGCTCTGTCTACCCCTTG
CTGGGTGGCAATGCCAATACTTCCGCTTTCTTTGATTCTATTTT
TATGTGTA
```

5. An isolated DNA as claimed in claim 1, in which the DNA segment coding for PACAP38 is a DNA segment coding for human PACAP38, said DNA segment comprising a nucleotide sequence having the following formula or a portion thereof which codes for a functional PACAP38:

6. An isolated DNA as claimed in claim 5, in which the DNA segment coding for human PACAP38 comprises a nucleotide sequence having the following formula or a portion thereof which codes for a functional PACAP38:

```
                                    5'  CAC  TCG  GAC  GGG  ATC
TTC  ACG  GAC  AGC  TAC  AGC  CGC  TAC  CGG  AAA  CAA  ATG  GCT  GTC  AAG
AAG  TAC  TTG  GCG  GCC  GTC  CTA  GGG  AAG  AGG  TAT  AAA  CAA  AGG  GTT
AAA  AAC  AAA  GGA  CGC  CGA  ATA  GCT  TAT  TTG  TAG  CGA  TGG  GTT  ACC
                                            ***
AGC  TAC  CCT  GTG  TAT  AC  3'
```

```
A   ATG  ACC  ATG  TGT  AGC  GGA  GCG  AGG  CTG  GCC  CTG  CTG  GTC  TAT
    GGG  ATA  ATC  ATG  CAC  AGC  AGC  GTC  TAC  AGC  TCA  CCT  GCC  GCC  GCC
    GGA  CTC  CGG  TTC  CCC  GGG  ATC  AGG  CCA  GAG  GAA  GAG  GCG  TAC  GGC
    GAG  GAC  GGA  AAC  CCG  CTG  CCA  GAC  TTC  GGT  GGC  TCG  GAG  CCG  CCG
    GGC  GCA  GGG  AGC  CCC  GCC  TCC  GCG  CCG  CGC  GCC  GCC  GCC  GCC  TGG
    TAC  CGC  CCG  GCC  GGG  AGA  AGA  GAT  GTC  GCC  CAC  GGG  ATC  CTT  AAC
    GAG  GCC  TAC  CGC  AAA  GTG  CTG  GAC  CAG  CTG  TCC  GCC  GGG  AAG  CAC
    CTG  CAG  TCG  CTC  GTG  GCC  CGG  GGC  GTG  GGT  GGG  AGC  CTC  GGC  GGC
    GGC  GCG  GGG  GAC  GAC  GCG  GAG  CCG  CTC  TCC  AAG  CGC  CAC  TCG  GAC
    GGG  ATC  TTC  ACG  GAC  AGC  TAC  AGC  CGC  TAC  CGG  AAA  CAA  ATG  GCT
    GTC  AAG  AAG  TAC  TTG  GCG  GCC  GTC  CTA  GGG  AAG  AGG  TAT  AAA  CAA
    AGG  GTT  AAA  AAC  AAA  GGA  CGC  CGA  ATA  GCT  TAT  TTG  TAGCGATGGGT
TACCAGCTACCCTGTGTATACAGCCCTGACGCAATGAAAAGTCGTTTTCCAAACTGAC
TCAACAGTCATCGCTCGTGTGTTCTATCCAAACATGTATTTATGTAATGAAGTAAAGCC
```

-continued

```
ATTAAATGAATATTTTGATAATAATATTGTTTTTCTTTCTACAAAGCACTAGAGAATGC
ACAGATATACTTTGTGGACCAATTATTGATATATATTATAAATATATATAAAGAATATA
TATATATATATATATAAAGTATAGAGAGAAGTTCATACAAAGCGTGCACAAGGATTG
AAAATTCGCCCGAGCTGTTTATGTTTTTATAAAAATAAATAGAAAAGTAGACAATCATT
GTTTTGAATATTACTCCTATTTTTGTAAACTGGAATTAAAAGGATAGTATTTTTATCCA
TGACAGGCCTGAAGATATTACTACTTACCATTTGCTACTGTACATAAACAATGATGCCC
TGCTCCAGGGAGATTTTGAGGTAAAGATATGGAGAATTGCTGAAGGGCATTCTTTCCCA
GTGAGTCTCTGGGGCAGGCTGCTTCAATCCCAGCCTAACTCAACTGGGCTCTGTCCCCC
TGGTTGGGTGGCAATTCCAATATTTCTGCTTTCTTTGATTCTCCTTTTATGTGTAGTTG
TCTCTCTTCAGACTCTCAGCCCAGAAGAAAATTCTCCTGATAAAACAACAGCTCGATCC
AAATTGTGCTTCTCCCCAGAATTCACGCCTCTCCCTAGGAGAAGAGTTGAGGAACTGTA
CAGAAAAGGGCGGCTTCGTTAGACCGCTCTCTTTTCTGTACTTCCTGAGTGGCCAGGGA
ATCTAATATCCCCAAATTAGGGCAATTGGAACAAAGTGAAGGACATAGAGGTATATTGG
AAGAGGCAGAGCCTGAGGTGGTAGGAGGAGGACCCTGGAAATGGACTGGTTTGAGATTG
CCCCAGGTCTGGGAAGCTGAGGGCAAATCCAGTCCCAGTGGTCCTGACTTTGGGCGCTG
GGTATTGGAAATGGATGCAAAGTACAATGTGTTTTTCTCCAGTGCTGTCCATGCTTCTC
ATCTTGTGAAATGGCCAGGATCCTCTCCTTTGAAACCTGCTCTGTAGGAGCTACCCTTT
TCCTTTGTGGTTTTATGGAGACCTCTCCTTCCTACCCTCCTGCACTGTTTAAGTACTGT
TTACCATTTTTCATTCACTTCTCTTAAACTTGTGAATGCTTCTCACTTTTTTTTTTTGT
TTGATGCAGGCACTTATTGTAAATTTTAGAAACCCCTCTGTAGCCACTAGTAAGTAATT
ATGCACTAAATATGAACCCTTTGTTTCTTGTTTATTGAGTTTGTAGGTAAAATGTATTT
TTCTACATTATTGCTTATTGCTTAGTAAAATTTATTTCATAAAA
```

7. An isolated DNA as claimed in claim 1, in which the DNA segment coding for PACAP38 is a DNA segment coding for rat PACAP38, said DNA segment comprising a nucleotide sequence having the following formula or a portion thereof which codes for a functional PACAP38:

```
                              CAC  TCG  GAC  GGC
ATC  TTC  ACA  GAC  AGC  TAT  AGC  CGC  TAC  CGA  AAA
CAA  ATG  GCT  GTC  AAG  AAA  TAC  TTG  GCG  GCC  GTG
CTA  GGG  AAA  AGG  TAT  AAA  CAG  AGG  GTT  AAA  AAC
AAA  GGA  CGC  CGA  ATA  GCG  TAC  TTG  TAG  GCATGAG
TTGCCAGCTACCGTGTGTATAAAATGAAAAGTCGTTTTCCAAAT
TGACTGACCAGTCATCACTCATGTGTTCTTTCCAAACATGTATT
TATGTATCAAGTAAAGCCATTAAATGACTATTTTGATAATAATA
TTGTTTTTCTTTTTACGAAGCACTGGAGAATGCACAGATATACT
TTGTGGACCAATTATTGATATATATTATAAGTATATATTAAGAA
TATATATAGGTATAGCAGAGAGCAATTCATAAGCGTGCACAAAG
ATTGAAAATTCGCCTGAGCTGTTTATGTTTTTATATAAAATGAA
TAGAGAAAATAGACAACCATTGTTTTGAATATTACTCCTATTTT
TGTAAACTGGAATTAAAGGATAGTATTTTTATCCACAACCGGCT
TGAAGATACCAATAATGGCCATTTGTACAAAAAAATGATGCCCT
GCTCCAGGAGAATTC
```

8. An isolated DNA as claimed in claim 7, in which the DNA segment coding for rat PACAP38 comprises a nucleotide sequence having the following formula or a portion thereof which codes for a functional PACAP38:

GAATTCAGGACTCTCAAAGCTCCACAATGGCGCCCAGCTCTCTC

CTCAGCAACAGACTGAAGGCTTCGGCTAGTTTTGTGCGTCTACA

AAGCTTTGAGCGGAATTTTAGCTTCGGCAAACAAGTCCCCCCAG

CTCCTCCAGCTAATTCCCGCGACTTCTCTCCAGACACCAGCTCC

AGACAGTGACTGATGCCTCTCTGGTTGTGATTCCAGCGCAGAAA

CTCGAAGGAGCCCTTTGCCCGCCGTCCTATTTAGTCAACTCTTT

| CCTAGCCGCGA | | ATG | ACC | ATG | TGT | AGC | GGA | GCA | AGG |
|---|---|---|---|---|---|---|---|---|---|
| TTG | GCC | CTG | TTG | GTC | TAC | GGG | ATA | ATA | ATG | CAT |
| AAC | AGC | GTC | TCC | TGT | TCA | CCT | GCC | GCC | GGA | CTC |
| AGC | TTC | CCT | GGG | ATC | AGA | CCA | GAA | GAA | GAG | GCT |
| TAC | GAT | CAG | GAC | GGA | AAC | CCG | CTG | CAA | GAC | TTC |
| TAC | GAC | TGG | GAC | CCT | CCG | GGC | GCA | GGG | AGC | CCC |
| GCC | TCC | GCG | CTG | CGT | GAC | GCC | TAC | GCC | CTT | TAC |
| TAC | CCA | GCC | GAC | AGG | AGA | GAT | GTC | GCC | CAC | GAA |
| ATC | CTT | AAC | GAA | GCC | TAC | CGC | AAA | GTC | TTG | GAC |
| CAG | CTG | TCC | GCC | AGG | AAG | TAC | CTG | CAG | TCC | ATG |
| GTG | GCC | AGG | GGC | ATG | GGC | GAG | AAC | CTC | GCC | GCC |
| GCC | GCG | GTG | GAC | GAC | CGG | GCA | CCC | CTT | ACC | AAA |
| CGC | CAC | TCG | GAC | GGC | ATC | TTC | ACA | GAC | AGC | TAT |
| AGC | CGC | TAC | CGA | AAA | CAA | ATG | GCT | GTC | AAG | AAA |
| TAC | TTG | GCG | GCC | GTG | CTA | GGG | AAA | AGG | TAT | AAA |
| CAG | AGG | GTT | AAA | AAC | AAA | GGA | CGC | CGA | ATA | GCG |
| TAC | TTG | TAG | CGATGAGTTGCCAGCTACCGTGTGTATAAAAT |

GAAAAGTCGTTTTCCAAATTGACTGACCAGTCATCACTCATGTG

TTCTTTCCAAACATGTATTTATGTATCAAGTAAAGCCATTAAAT

GACTATTTTGATAATAATATTGTTTTTCTTTTTACGAAGCACTG

GAGAATGCACAGATATACTTTGTGGACCAATTATTGATATATAT

TATAAGTATATATTAAGAATATATATAGGTATAGCAGAGAGCAA

TTCATAAGCGTGCACAAAGATTGAAAATTCGCCTGAGCTGTTTA

TGTTTTTATATAAAATGAATAGAGAAAATAGACAACCATTGTTT

TGAATATTACTCCTATTTTTGTAAACTGGAATTAAAGGATAGTA

TTTTTATCCACAACCGGCTTGAAGATACCAATAATGGCCATTTG

TACAAAAAAATGATGCCCTGCTCCAGGAGAATTC

9. A transformant containing an isolated DNA comprising a DNA segment coding for PACAP38.

10. A transformant containing the DNA as claimed in claim 3 or 4.

11. A transformant of claim 10 having the characteristics of E. coli DH5α/pOH38P7 (FERM BP-2484).

12. A method for preparing a mature PACAP38 protein comprising cultivating the transformant as claimed in claim 10, producing and accumulating the mature PACAP38 protein in a culture, and collecting the protein.

13. A host transformed with the isolated DNA as claimed in claim 5 or 6, thereby forming a transformant.

14. A transformant of claim 23 having the characteristics of E. coli DH5α/pHT38P8 (FERM BP-2622).

15. A method for preparing a mature PACAP38 protein comprising cultivating the transformant as claimed in claim 23, producing and accumulating the mature PACAP38 protein in a culture, and collecting the protein.

16. A host transformed with the isolated DNA as claimed in claim 7 or 8, thereby forming a transformant.

17. A transformant of claim 16 having the characteristics of *E. coli* JM109/pRB38P21 (FERM BP-2762).

18. A method for preparing a mature PACAP38 protein comprising cultivating the transformant as claimed in claim 16, producing and accumulating the mature PACAP38 protein in a culture, and collecting the protein.

* * * * *